United States Patent [19]

Barton et al.

[11] 4,174,318

[45] Nov. 13, 1979

[54] ALKYLATIVE CLEAVAGE OF AZETIDINONE DISULFIDES

[75] Inventors: Derek H. R. Barton; Peter G. Sammes, both of London; Graham Hewitt, Northolt; Brian E. Looker, Greenford; William G. E. Underwood, Stoke Poges, all of England

[73] Assignee: Glaxo Laboratories Ltd., Great Britain

[21] Appl. No.: 726,425

[22] Filed: Sep. 22, 1976

Related U.S. Application Data

[60] Continuation of Ser. No. 389,663, Aug. 30, 1973, abandoned, which is a division of Ser. No. 167,875, Jul. 30, 1971, abandoned.

[30] Foreign Application Priority Data

Nov. 3, 1970 [GB] United Kingdom ............... 52286/70

[51] Int. Cl.$^2$ .................. C07D 205/08; C07D 499/00
[52] U.S. Cl. .............................. 260/239 A; 260/245.2; 260/245.4; 260/345.7 R; 260/345.8 R
[58] Field of Search ............. 260/239 A, 345.7, 345.8

[56] References Cited

U.S. PATENT DOCUMENTS

| 3,872,086 | 3/1975 | Barton et al. ..................... 260/239 A |
| 3,880,833 | 4/1975 | Scartazzini et al. ............. 260/239 A |

OTHER PUBLICATIONS

Schönberg et al. I, Chem. Ber. 62, 440-441 (1929).
Jacobson et al., J. Amer. Chem. Soc. 77, 6064-6065 (1955).
Fromm et al., Chem. Abs. 7, 1001 (1913).
Schönberg et al. II, Chem. Ber. 66, 237-244 (1933).
Schönberg, et al. III, J. Chem. Soc. 1949, pp. 892-893.
3,993,646 11001976 Kamiya et al. 260 239 A

*Primary Examiner*—Mark L. Berch
*Attorney, Agent, or Firm*—Bacon & Thomas

[57] ABSTRACT

Novel semisynthetic 4-thio-azetidin-2-one derivatives of use in the production of cephalosporins, penicillins and related β-lactam antibiotic compounds are provided by cleavage reactions involving the corresponding 4-dithio-azetidin-2-one derivative or a suitable thiazoline derivative, which starting materials may be obtained from penicillins without changing the configuration of the β-lactam structure desired in the final product.

9 Claims, No Drawings

ALKYLATIVE CLEAVAGE OF AZETIDINONE DISULFIDES

This is a continuation, of application Ser. No. 389,663, filed Aug. 30, 1973, now abandoned, which in turn is a divisional of application Ser. No. 167,875 filed July 30, 1971, now abandoned.

This invention relates to novel semisynthetic intermediates or relay compounds of use in the production of cephalosporins, penicillins and related β-lactam antibiotic compounds.

The first total synthesis of a cephalosporin antibiotic was achieved by R. B. Woodward (J.A.C.S. 1966, 88, (4), 852) starting from L(+)-cysteine and proceeding via about eight synthetic steps to a β-lactam (i) which was then converted into a cephem (iii) by the following reaction sequence.

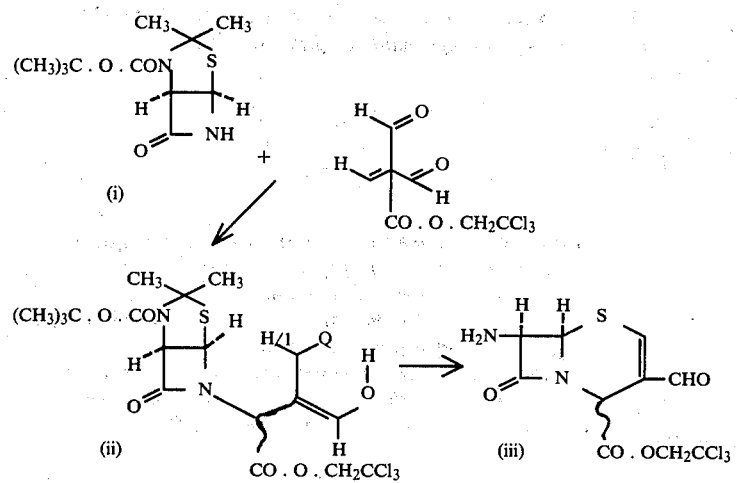

The compound (i) thus constitutes a valuable intermediate in the preparation of cephalosporins and other β-lactam antibiotics; by reaction with an analogous aldehyde reagent it is also possible to convert (i) into a penicillin and it will be appreciated that in this way penicillins having varying substitution in the 5-membered ring can be produced. Similarly by replacing the 2,2,2-trichloroethyl 3,3-diformylacrylate reagent by suitably substituted alternatives, a series of cephalosporin analogues can be prepared.

R. B. Woodward started from L(+)-cysteine in order to achieve a total synthesis. However, this material is relatively expensive and even more significantly, its conversion into a β-lactam of the required stereochemical configuration requires extremely careful control of the stereochemistry at several points. We have now found that intermediates analogous to Woodward's compound (i) can be produced from penicillins, while retaining the steric configuration common to the β-lactam rings of both the cephalosporins and the penicillins and so requiring substantially less control of the stereochemistry during the overall synthesis. Furthermore, penicillins, particularly penicillins G and V, are generally cheaper to produce, e.g. by fermentation, than L(+)-cysteine.

The copending applications of Barton, Long, Looker, Wilson and Underwood U.S. patent application Ser. No. 167,876, filed July 30, 1971, now abandoned in favor of a pending divisional application filed on Aug. 12, 1976, Ser. No. 713,649 and Underwood and Hewitt U.S. patent application Ser. No. 167,847, filed July 30, 1971, which has been refiled as Continuation Application Ser. No. 448,624, which has been refiled as continuation application Ser. No. 619,233, filed Oct. 3, 1975, now abandoned respectively describe the cleavage of the 1,2-bond or certain penicillin derivatives to yield thiazolines of the general formula

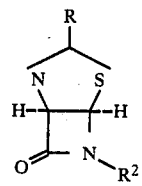

where R is hydrogen or the residue of the 6-acylamino side chain of the penicillin while $R^2$ is hydrogen or a residue derived from the thiazolidine ring of the penicillin. The cleavage of the penicillin 1,2-bond results in "trapping" of the sulphur by the carbonyl group of the 6-acylamino group to form the thiazoline ring structure. The compounds in which $R^2$ is hydrogen can, if desired, be reacted with reagents introducing at the β-lactam nitrogen a group ultimately capable of cylising with the sulphur atom or a group attached thereto. These compounds can be reduced and N-acylated as described in the copending application of Underwood and Long U.S. patent application Ser. No. 167,874, filed July 30, 1971, which issued as U.S. Pat. No. 3,900,487 on Aug. 19, 1975 to yield thiazolidines which undergo exactly the same reactions as Woodward's Compound (i).

The copending application of Barton, Taylor, Underwood, Looker and Hewitt U.S. Pat. application No. 167,848, filed on July 30, 1971, which issued as U.S. Pat. No. 3,872,086 on Mar. 18, 1975 describes the "trapping" of the penicillin sulphur atom by an external thiophile after cleavage of the 1,2-bond yielding β-lactams of the general formula

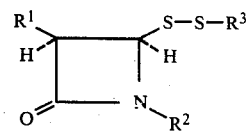

where $R^1$ is a group —NHCOR, R has the above meaning and $R^2$ is hydrogen or an aliphatic, araliphatic or aromatic group, including residues derived from the thiazolidine ring of a penicillin and $R^3$ is the residue of a thiophilic sulphur nucleophile. We have therein further described the oxidation of thiazolines of formula I to form symmetrical disulphides of formula II in which $R^3$ is a group of the formula

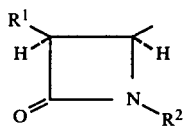

where $R^1$ and $R^2$ have the above meanings.

The present invention is concerned with the cleavage of disulphides of formula II to form thioethers or thioesters which may be subjected to cyclisation to form polycyclic structures such as cephams, cephems or penams, or indeed may themselves include such a structure. Thus, the disulphides can be subjected to cleavage of the S—S—bond and capture of the sulphur attached to the β-lactam ring to give a compound of the formula

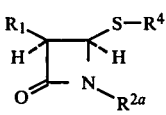

where $R^{2a}$ will in general be identical with $R^2$, no modification of the grouping having taken place, but if $R^2$ carries a substituent capable of cyclising spontaneously with the sulphur atom immediately after cleavage, $R^{2a}$ may then constitute with $R^4$ a divalent hydrocarbyl group as is indicated in the detail hereinafter; and $R^4$ is an aliphatic, araliphatic, cycloaliphatic or aromatic hydrocarbyl or acyl group, or forms with $R^{2a}$ a divalent hydrocarbyl grouping. The above hydrocarbyl group may be substituted or unsubstituted.

Advantageously the monovalent groups $R^4$ may either carry a functional grouping capable of reacting with the β-lactam nitrogen when the latter is in the unblocked form or such a group may be introduced later, for example by conventional functionalisation techniques such as bromination. Where $R^4$ is a 2-tosyloxy-2-carboxyethyl group, preferably in esterified form (which may, for example, be introduced by cleavage of a disulphide of formula II in the presence of a 2-bromo-1-hydroxy-propionic acid ester), subsequent condensation with the β-lactam nitrogen will yield a 3-carboxy-penam. If the S-carboxy-ethyl group carries substituents, various 3-carboxy-penam analogues of the natural penicillins can be produced having "unnatural" substitution in the thiazolidine ring.

It should further be noted that the cleavage reactions described herein, whereby the S-atom in "trapped" form is liberated, when effected on compounds in which the group $R^2$ carries a reactive functional group, can produce bicyclic compounds of the penam and cepham type directly. Thus, for example, when $R^2$ in formula II is an esterified 2-bromo-2-carboxyethyl group cleavage yields a product of formula IV in which $R^{2a}$ and $R^4$ form a chain

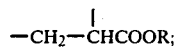

subsequent deesterification yields a 2-carboxypenam, a class of penams which shows antibiotic activity. Thus, compounds of formula II in which $R^1$ is the phenylacetamido group, $R^3$ is an isobutyl group and $R^2$ is a 2-methoxycarbonyl or 2-p-phenoxycarbonyl-2-bromoethyl group may be cleaved to yield the corresponding esters of 6-phenylacetamido-penam-2-carboxylic acid which has been shown to exhibit antibiotic activity. It will be appreciated that in all these reactions the group $R^1$ may be one of the acylamino groups present in known penicillin antibiotics, for example the phenylacetamino group.

One object of the present invention is to modify penicillins to give other bicyclic structures.

According to one feature of the invention there are provided compounds of general formula IX

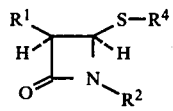

wherein $R^1$ is an amino or blocked amino group, $R^2$ is a hydrogen atom or an aliphatic, araliphatic or aromatic group and $R^4$ is an aliphatic, araliphatic, cycloaliphatic or aromatic hydrocarbyl group except that $R^4$ is not an isopropyl, isopropenyl or substituted isopropyl or isopropenyl group when $R^2$ is hydrogen or a formyl group.

The invention also provides a process for the preparation of compounds of general formula IV

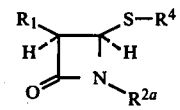

wherein $R^1$ is as defined above for formula IX, $R^4$ is an aliphatic, araliphatic, cycloaliphatic or aromatic hydrocarbyl or acyl group and $R^{2a}$ is a hydrogen atom or an aliphatic, araliphatic or aromatic group, or $R^{2a}$ and $R^4$ together form a divalent hydrocarbyl group, which comprises subjecting the —S—S— bond of a disulphide of formula II

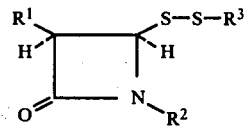

wherein $R^2$ is a hydrogen atom or an aliphatic, araliphatic or aromatic group and $R^3$ is the residue of a thiophilic sulphur nucleophile to cleavage in the presence of a reagent serving to introduce the said group $R^4$.

The —S—S— bond may be subjected to reductive cleavage in the presence of an S-etherifying or S-esterifying reagent serving to introduce the group $R^4$. In general the reagent will be of the general formula $R^4X$ where $R^4$ has the above meaning and X is a reactive ester group. X may thus be a halogen atom such as a chlorine, bromine or iodine atom or an aromatic or aliphatic sulphonyloxy group such as a tosyloxy or mesyloxy group.

The group $R^2$ in compounds of formula II may effectively act as the S-etherifying or S-esterifying reagent when $R^2$ carries a reactive ester group, this providing a means of cyclisation whereby compounds of formula IV in which $R^4$ and $R^{2a}$ together form a divalent hydrocarbyl grouping may be obtained.

Reductive cleavage of the —S—S— bond may be effected for example by reducing agents or electrolysis, whereby electrons are introduced, or by a thiophilic nucleophile which also provides electrons; in such a case a transient intermediate is though to be the thiolate anion which reacts subsequently with the etherifying agent.

Thus, for example, the disulphide of formula II can be reacted with a trivalent phosphorus compound to effect the desired cleavage. This reagent can be represented as $PR^5R^6R^7$ where $R^5$ and $R^6$, which may be the same or different, are hydrocarbyl, hydrocarbyloxy or hydrocarbylamino groups, e.g. alkyl, alkoxy or dialkylamino groups, preferably having 1–6 carbon atoms such as methyl, ethyl, t-butyl, methoxy or ethoxy groups; aralkyl, aralkoxy or diaralkylamino groups, preferably monocyclic groups with 1–6 carbon atoms in the alkyl portion, such as benzyl, phenethyl, benzyloxy or phenethoxy groups; or aromatic groups, preferably monocyclic groups, such as phenyl, tolyl, phenoxy or tolyloxy groups or diarylamino groups; or $R^5$ and $R^6$ may together with the phosphorus atom form a ring; and $R^7$ is another group as defined for $R^5$ and $R^6$ or a hydroxyl group. Particular reagents of this type are the di- and tri- alkyl phosphites, preferably the latter, and the trisubstituted phosphines; convenient reagents are tri-n-butyl and tri-n-octyl phosphines and trimethyl and triethyl phosphite. The compound $P(NMe_2)_3$ is a convenient reagent of the tri(hydrocarbylamino)phosphine type.

It should be noted that the above phosphites can themselves act as S-etherifying agents in that they are reactive ester derivatives of alcohols or phenols. Thus, for example, reaction of trimethyl phosphite with the disulphide will give a methyl derivative of formula IV with $R^4$ being $CH_3$—. By providing the phosphite reagent with appropriate substituents produced of formula IV can be obtained in which $R^4$ is a chain carrying substituents able to cyclise directly with the β-lactam nitrogen or a group attached thereto.

A still further possibility is that the cleavage of the —S—S— bond by the trivalent phosphorus reagent will add on to the reagent the cleaved fragment —$SR^4$ to form a phosphonium cation $R^3$—S—P+$R^5R^6R^7$ which will then act as the S-etherifying reagent to yield a product of formula IV in which $R^4$ is identical with $R^3$.

Where the group $R^2$ carries a sustituent capable of effecting cyclisation with the initially formed thiolate ion, a product of formula IV in which $R^{2a}$ and $R^4$ constitute a divalent group may be formed directly, for example a cepham or penam.

The reaction with phosphorus-based reagents is preferably effected at between 0° and 120° C., conveniently in the range 15° to 50° C.

The S-etherifying reagent may in some cases serve as solvent, where it is liquid, but in general an inert solvent is preferably present, for example a cyclic ether solvent such as dioxan or tetrahydrofuran, an ester solvent such as ethyl acetate, or a hydrocarbon solvent such as benzene or toluene. A small quantity of a hydroxylic substance is preferably present e.g. water.

Selective reduction of the —S—S— bond can also be effected using electrolysis or reagents such as hydrogen iodide or more particularly, hydride reducing agents. Such reagents should not attack other parts of the molecule and we have found borohydrides especially suitable, particularly alkali metal borohydrides such as sodium or potassium borohydride. Borohydrides may be used in hydroxylic solvents such as alkanols, e.g. methanol, ethanol etc. and/or water.

Cleavage can also be effected using thiophilic sulphur nucleophiles and in particular thiols, including substances such as thiourea and other thioamides, thiophosphates, thiosulphates, sulphites, sulphinates, thiocyanates and thioglycollates which can react as thiols, and hydrogen sulphide. The thiols or hydrogen sulphide are preferably reacted either in the presence of a base or as salts with bases. Such bases include inorganic bases, in particular alkali metal compounds e.g. sodium, potassium or lithium compounds, for example hydroxides, alkoxides, and hydrides and organic bases such as amines e.g. triethylamine or quaternary ammonium hydroxides. The sulphur nucleophiles can be represented by the general formula $R^3SH$ where $R^3$ has the above meaning, other than a group of formula III. Cleavage can additionally be effected by cyanides. The foregoing thiophosphates, thiosulphates, sulphites, sulphonates, thiocyanates and cyanides are preferably alkali metal, e.g. sodium or potassium, or quaternary ammonium salts.

It should be noted that the above reductive cleavage reactions and the cleavage with a sulphur nucleophile cleave the disulphide selectively to introduce the group $R^4$ in the desired manner.

Alternatively cleavage of the —S—S— bond in the disulphides of formula II may be effected by oxidation whereby an electron deficient species such as a cation of the formula $R^8S^+$ is generated, where $R^8$ is a group of the formula III as defined above. This cation will in general react with the predominant anionic species present to form a sulphenyl derivative. Thus, for example, oxidation with chlorine, bromine or iodine, advantageously in the presence of an inert solvent such as a halogenated hydrocarbon, e.g. a carbon tetrahalide, yields a sulphenyl halide. The sulphenyl halide may then be reacted with an unsaturated aliphatic or cycloaliphatic hydrocarbon e.g. an alkene, or cycloalkene for example ethylene or cyclohexene, to add across a double-bond thereof yielding a β-haloalkyl sulphide of formula $R^8$—S—$R^9$—Hal where $R^8$ represents a group of formula III, $R^9$ represents a divalent aliphatic or cycloaliphatic group and Hal represents a chlorine, bromine or iodine atom. The aliphatic or cycloaliphatic hydrocarbon, and hence the group $R^9$, may carry substituents such as aromatic rings or other substituents as specifically described hereinafter in relation to $R^3$.

Where $R^3$ in the compound of Formula II is a group of formula III, cleavage may not always be symmetrical and consequently, one of the two β-lactam rings may be wasted. In general, however, reduction will yield two thiolate anions. Reaction with a dialkali metal sulphide will normally yield initially a mixture of alkali metal thiolate $R^8SAlk$. and $R^8$—S—S—Alk., where Alk. represents an alkali metal and $R^8$ represents a group of formula III, the latter compound rearranging at least in part, to give the corresponding thiolate $R^8SAlk$. and sulphur. The reaction may thus yield more than half the original β-lactam content as the desired thiolate for S-etherification or S-esterification.

The thioethers of formula IV, which are key intermediates in the conversion of penicillins into cephalosporins or modified penicillins, can also be prepared by S-etherification or S-esterification of thiazolines of general formula I.

Thus we have found that reaction of the thiazoline I with an S-esterifying or S-etherifying reagent preferably in the presence of a thallium triacylate or a weak base having a pKa of less than 10 (in water at 25° C.), e.g. urea, and a hydroxylated compound yields a compound of formula IV in which $R^1$ is —NHCOR as defined above and $R^{2a}$ has the above meaning. The reagent may be for example a compound of the formula $R^{4a}X$ where $R^{4a}$ carries an electron withdrawing group in the α-position e.g. a carbonyl group as in an α-haloester or α-haloketone, for example ethyl bromoacetate, α-bromoacetone or phenacyl bromide, and X is a reactive ester group.

Where the hydroxylated compound produces ions other than hydroxyl ions, the initial product may, in the absence of water, be an imino ether rather than an amide of formula IV and treatment with a protic solvent such as water will be required to generate the amide. The hydroxylated compound may, for example, be an alkanol such as methanol or ethanol. In general, it is preferred that sufficient water should be present during the reaction to form the amide directly. Suitable solvent media include alkanols such as ethanol or methanol, ketones such as acetone or methyl ethyl ketone, cyclic ethers such as dioxan or tetrahydrofuran or amide, imide or hydantoin solvents such as dimethylformamide and dimethylacetamide.

The group $R^{4a}$ in the esterifying or etherifying reagent $R^{4a}X$ is advantageously one which can be made to cyclise ultimately with the β-lactam nitrogen or with a group attached thereto; thus for example, useful reagents of the formula $R^{4a}X$ include α-halo-acetic esters such as ethyl bromoacetate, 1-halo-ketones such as bromoacetone or phenacyl bromide, αβ-dihalo-propionic esters such as methyl or p-nitrobenzyl αβ-dibromopropionate, α-halo-acrylic esters such as methyl and p-nitrobenzyl α-bromoacrylates and acyl halides such as aliphatic, araliphatic or aromatic acyl halides e.g. acetyl bromide.

The thallium triacylate may be derived from aliphatic, araliphatic or aromatic carboxylic acids but is preferably thallium triacetate. The weak base incorporated as an alternative to the thallium triacylate may, for example, be a weak base such as urea.

The compounds of formula IV in which $R^{2a}$ is hydrogen and $R^4$ is an acyl group may also be prepared by reaction of a penam 1-oxide of the formula

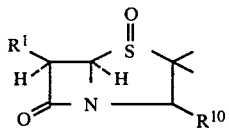

VII where $R^1$ has the above meaning and $R^{10}$ is a hydroxyl or amino group or a protected hydroxyl or amino group, with a trivalent phosphorus compound in the presence of an anhydride or mixed anhydride of a carboxylic acid to produce a compound of the formula

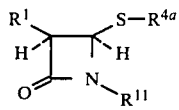

VIII where $R^{4a}$ is an acyl group and $R^{11}$ is hydrogen or a group

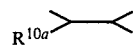

where $R^{10a}$ is a protected hydroxyl or amino group, followed by conversion of said protected group, where present, to a hydroxyl or amino group with consequent replacement of the group

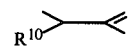

by hydrogen.

The anhydrides used in the above reaction may be symmetrical anhydrides or unsymmetrical anhydrides in which the acyl group is joined to an acyloxy group derived from another acid, e.g. a carboxylic or sulphonic acid. The acyl group $R^{4a}$ preferably carries grouping suitable for subsequent cyclisation, as set out hereinafter. Simpler acyl groups, such as acetyl groups are also useful, however, in that they may subsequently be cleaved in the presence of reagents serving to introduce more elaborate side-chains capable of cyclisation to give the desired rings and such simple acyl groups thus serve to trap and protect the S-atom.

The group $R^{10}$ is a hydroxyl or amino group or a protected hydroxyl or amino group, that is a group which may be converted to hydroxyl or amino without unwanted degradation of other parts of the molecule, for example by mild acidic or basic hydrolysis, enzymic hydrolysis or hydrogenolysis. Suitable protected hydroxyl groups include, for example, readily cleaved ether and ester groups set out hereinafter for $R^m$ in formula V. The esterifying grouping in the urethanes may, for example, by any alcohol residue which can readily be cleaved from the urethane, as set out hereinafter for $R^m$ in formula V.

In the above formulae in general, $R^1$ represents an amino group or a blocked amino group, including the 6-acylamino groups present in penicillins, which may be represented as —NHCOR.

Typical protected amino groups are illustrated in the following table:

| Type | Example | Usual Name and Analogues etc. |
|---|---|---|
| Urethane | HNCOCH$_2$Phenyl ‖ O | Benzyloxycarbonyl, p-Methoxy |
| Urethane | HNCOC(CH$_3$)$_3$ ‖ O | t-Butoxycarbonyl |
| Urethane | HNCOCHPh$_2$ ‖ O | Diphenylmethoxycarbonyl |

-continued

| Type | Example | Usual Name and Analogues etc. |
|---|---|---|
| Urethane | HNCO-(1-adamantyl) with ‖O | 1-Adamantyloxycarbonyl |
| Aryl-methyl-amino | HNCPh₃ | Trityl |
| Onium | NH₃ + | |
| Urethane | HN.CO.OCH₂CCl₃ | β,β,β-trichloroethoxy-carbonyl |

In the aforementioned chain —NHCOR the group R can be hydrogen or any grouping present in the 6-acylamino side chain of a penicillin and in general will remain unchanged in the reaction sequence although modification to the chain may not be undesirable in the final product. R can be defined generally as hydrogen or an organic group which preferably contains 1-20 carbon atoms.

A wide range of substituents may be present. In general, the following main clases are specially suitable for the acyl group RCO:

(i) $R^u C_n H_{2n}$—CO where $R^u$ is an aryl (carbocyclic or heterocyclic), cycloalkyl, substituted aryl, substituted cycloalkyl, cyclohexadienyl or non-aromatic or mesoionic heterocyclic group, and n is an integer from 1-4. Examples of this group include phenylacetyl; substituted phenylacetyl e.g. aminophenylacetyl, acetoxyphenylacetyl, methoxyphenylacetyl, fluorophenylacetyl, nitrophenylacetyl, methylphenylacetyl, or hydroxyphenylacetyl; N,N-bis(2-chloroethyl)aminophenylpropionyl; thienyl-2- and -3-acetyl; 4-isoxazolyl and substituted 4-isoxazolylacetyl; pyridylacetyl; tetrazolylacetyl or a sydnoneacetyl group. The substituted 4-isoxazolyl group may be a 3-aryl-5-methyl-isoxazol-4-yl group, the aryl group being e.g. phenyl or halophenyl e.g. chloro- or bromophenyl. An acyl group of this type is 3-o-chlorophenyl-5-methylisoxazol-4-yl-acetyl.

(ii) $C_n H_{2n+1}$CO— where n is an integer from 1-7. The alkyl group may be straight or branched and, if desired, may be interrupted by an oxygen or sulphur atom or substituted by e.g. one or more halogen atoms a cyano group, a carboxy group, an alkoxycarbonyl group, a hydroxy group or a carboxycarbonyl group (—CO.COOH). Examples of such groups include cyanoacetyl, hexanoyl, heptanoyl, octanoyl, butylthioacetyl, chloroacetyl and trichloroacetyl groups.

(iii) $C_n H_{2n-1}$CO— where n is an integer from 2-7. The alkenyl group may be straight or branched and, if desired, may be interrupted by an oxygen or a sulphur atom. An example of such a group is allylthioacetyl.

(iv)

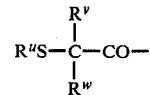

where $R^u$ has the meaning defined under (i) and in addition may be benzyl, and $R^v$ and $R^w$ which may be the same or different each represent hydrogen, phenyl, benzyl, phenethyl or lower alkyl. Examples of such groups include phenoxyacetyl, 2-phenoxy-2-phenylacetyl, 2-phenoxypropionyl, 2-phenoxybutyryl, 2-methyl-2-phenoxy-propionyl, p-cresoxyacetyl and p methylthiophenoxvacetyl.

(v)

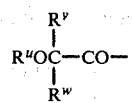

where $R^u$ has the meaning defined under (i) and, in addition, may be benzyl and $R^v$ and $R^w$ have the meanings defined under (iv). Examples of such groups include S-phenylthioacetyl, S-chlorophenylthioacetyl, S-fluorophenylthioacetyl, pyridylthioacetyl, and S-benzylthioacetyl.

(vi) $R^u Z(CH_2)_m CO$— where $R^u$ has the meaning defined under (i) and, in addition, may be benzyl, Z is an oxygen or sulphur atom and m is an integer from 2-5. An example of such a group is S-benzylthiopropionyl.

(vii) $R^u CO$— wherein $R^u$ has the meaning defined under (i). Examples of such groups include benzoyl, substituted benzoyl (e.g. aminobenzoyl), 4-isoxazolyl- and substituted 4-isoxazolyl carbonyl, cyclopentanecarbonyl, sydnonecarbonyl, naphthoyl and substituted naphthoyl (e.g. 2-ethoxynapthoyl)quinoxalinylcarbonyl and substituted quinoxalinylcarbonyl (e.g. 3-carboxy-2-quinoxalinylcarbonyl). Other possible substituents for benzoyl include alkyl, alkoxy, phenyl, phenyl substituted by carboxy, alkylamido, cycloalkylamido, allylamido, phenyl(lower)alkyl amido, morpholinocarbonyl, pyrrolidinocarbonyl, piperidinocarbonyl, tetrahydropyridino, furfurylamido or N-alkyl-N-anilino, or derivatives thereof and such substituents may be in the 2- or 2- and 6-positions. Examples of such substituted benzoyl groups are 2,6-dimethoxybenzoyl, 2-methylamidobenzoyl and 2-carboxybenzoyl. Where the group $R^u$ represents a substituted 4-isoxazolyl group, the substituents may be as set out above under (i). Examples of such 4-isoxazolyl groups are 3-phenyl-5-methyl-isoxazol-4-yl carbonyl, 3-o-chlorophenyl-5-methyl-isoxazol-4-yl carbonyl and 3-(2,6-dichlorophenyl)-5-methyl-isoxazol-4-yl carbonyl.

(viii)

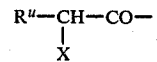

where $R^u$ has the meaning defined under (i) and X is amino, substituted amino (e.g. acylamido or a group obtained by reacting the α-aminoacylamido group of the 6-side chain with an aldehyde or ketone e.g. acetone, methylethylketone or ethyl acetoacetate), hydroxy, carboxy, esterified carboxy, triazolyl, tetrazolyl, cyano, halogeno, acyloxy (e.g. formyloxy or lower alkanoyloxy) or etherified hydroxy group. Examples of such acyl groups are α-aminophenylacetyl and α-carboxyphenylacetyl.

(ix)

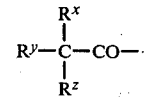

where $R^x$, $R^y$ and $R^z$ which may be the same or different may each represent lower alkyl, phenyl, or substituted phenyl. $R^x$ can also be hydrogen. An example of such an acyl group is triphenylmethylcarbonyl.

(x)

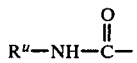

where $R^u$ has the meaning defined under (i) and in addition may be hydrogen, lower alkyl or halogen substituted lower alkyl. An example of such a group is $Cl(CH_2)_2NHCO$.

(xi)

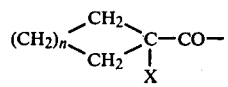

where X has the meaning defined under (viii) above and n is an integer of from 1 to 4. An example of such an acyl group is 1-aminocyclohexane-carbonyl.

(xii) Amino acyl, for example $R^wCH(NH_2).(CH_2)_nCO$ where n is an integer from 1–10, or $NH_2. C_nH_{2n}Ar(CH_2)_mCO$, where m is zero or an integer from 1–10, and n is 0, 1 or 2, $R^w$ is a hydrogen atom or an alkyl, aralkyl or carboxy group or a group as defined under $R^u$ above, and Ar is an arylene group, e.g. p-phenylene or 1,4-naphthylene. Examples of such groups are disclosed in British Patent Specification No. 1,054,806. A group of this type is the p-aminophenylacetyl group. Other acyl groups of this type include those, e.g. δ-aminoadipoyl, derived from naturally occurring amino acids and derivatives thereof e.g. N-benzyl-δ-aminoadipoyl or N-chloroacetyl-δ-aminoadipoyl.

(xiii) Substituted glyoxylyl groups of the formula $R^y.CO.CO-$ where $R^y$ is an aliphatic, araliphatic or aromatic group, e.g. a thienyl group, a phenyl group, or a mono-, di- or tri- substituted phenyl group, the substituents being, for example, one or more halogen atoms (F, Cl, Br, or I), methoxy groups, methyl groups or amino groups, or a fused benzene ring. Included in this group are also the α-carbonyl derivatives of the above substituted glyoxylyl groups, formed for example with hydroxylamine, semicarbazide, thiosemicarbazide, isoniazide or hydrazine.

Preferred amine protecting groups are the hydrocarbyloxycarbonyl groups (wherein the amino group forms part of a urethane), in particular alkoxycarbonyl groups such as methoxycarbonyl, ethoxycarbonyl and, most preferably, t-butoxycarbonyl groups, which may carry substituents such as halogen atoms as in the 2,2,2-trichloroethoxycarbonyl group, as well as aralkoxycarbonyl groups such as benzyloxycarbonyl, p-methoxybenzyloxycarbonyl and diphenylmethoxycarbonyl groups. Cycloalkoxycarbonyl groups are also advantageous, especially the adamantyloxycarbonyl group. The p-nitrobenzyloxycarbonyl groups which can be selectively removed by reduction e.g. hydrogenolysis, is also useful. It will be appreciated that such penicillins carrying protecting groups of this type may be prepared from 6-aminopenams by conventional methods for example by reaction with an appropriate haloformic ester.

The group $R^2$ is hydrogen or an aliphatic, araliphatic or aromatic group, for example a group derived from the thiazolidine ring of penicillin as described in our said copending British Patent Applications.

Thus for example, $R^2$ can be a group of the formula

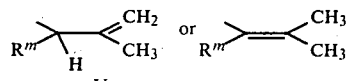

where $R^m$ is a hydrogen atom, an esterified or etherified hydroxyl group; an acylamino group, e.g. a urethane group; a carboxyl group or an esterified carboxyl group. $R^2$ can also be a pyrazoline derivative of a group of formula VI.

Where $R^m$ is an etherified or esterified hydroxyl group the O- attached grouping is preferably readily cleaved to hydroxyl, for example by mild acidic, basic or enzymic hydrolysis, reduction or hydrogenolysis to permit removal of the whole chain on the β-lactam nitrogen. Such removable groups include, in particular, the tetrahydropyranyloxy, 4-methoxy-tetrahydropyranyloxy, di-(2-chloroethoxy)-methoxy, di-phenylmethoxy, carbobenzoxy or trifluoroacetoxy groups. Where $R^m$ is a urethane or esterified caroxyl group the terminal alcohol or phenol residue is preferably one which is readily cleaved by acidic, basic or enzymic hydrolysis or reduction or hydrogenolysis. Such alcohol residues include, in particular, 2-halo-lower alkyl groups, preferably carrying more than one halogen atom, for example a 2,2,2-trichloroethoxy or 2,2,2-trichloro-1-methyl-ethoxy group or a 2,2,2-tribromoethoxy group; or a 2-iodoethoxy group. These groups may readily be removed by reduction. The alcohol residue may also be an arylmethyl group such as a benzyl group which may be removed by hydrolysis.

$R^2$ can also be an aliphatic, araliphatic or aromatic group other than the residue of a thiazolidine ring; such groups can, for example, be introduced prior to the sulphur cleavage by reaction of compounds of formula II (or precursors thereof) in which $R^2$ is hydrogen with a reactive ester, e.g. a halide, of an alcohol or phenol, preferably in the presence of a strong base. Such groups advantageously carry functional substituents which will permit cyclisation of the compound when the disulphide is cleaved to yield a polycyclic structure such as a further penicillin or a cephalosporin. Such functional substituents include, in particular, reactive ester substituents such as halogen atoms and aliphatic or aromatic sulphonyloxy groups. $R^2$ may also conveniently carry inert substituents such as esterified carboxyl groups, e.g. p-nitrobenzyloxycarbonyl or phenacyloxy-carbonyl groups.

The group $R^3$ in the disulphide starting material is preferably a grouping of the formula III or the residue of a thiol, preferably an aliphatic, araliphatic, cycloaliphatic or aromatic group, which advantageously contains 1–20 carbon atoms. $R^3$ may thus, for example, be an alkyl group, preferably containing 1–6 carbon atoms, e.g. a methyl, ethyl, butyl or iso-butyl group; an aralkyl group, preferably containing 1–6 carbon atoms in the alkyl portion, e.g. a benzyl, phenylpropyl group; a cycloalkyl group which may contain 5–7 carbon atoms in the ring and in which other aliphatic ring substituents containing up to 6 carbon atoms may be present; a monocyclic aryl group such as a phenyl or substituted phenyl group. Such groups may be saturated or unsaturated and may carry substituents. As is explained above, the group $R^3$ may become the group $R^4$ of the compound of formula IV and may advantageously possess substituents or reactive bonds permitting cyclisation with the β-lactam nitrogen or a group attached thereto. Such substituents include reactive ester substituents, for example, halogen atoms and aromatic and aliphatic sulphonyloxy groups, carboxyl or esterified carboxyl groups or amino groups.

The group $R^4$ in the product of formula IV may be an aliphatic, araliphatic, cycloaliphatic or aromatic group advantageously containing 1–20 carbon atoms and may, for example, be an alkyl group, which may contain, for example, 1–6 carbon atoms, e.g. a methyl, ethyl or butyl group; an aralkyl group, preferably a monocyclic group having 1–6 carbon atoms in the alkyl portion, e.g. a benzyl, phenethyl or phenylpropyl group; or a cycloalkyl group such as a 1-ethyl or 1-propyl-cyclohexyl or cyclopentyl group. To effect subsequent cyclisation the group $R^4$ must ultimately be functionalised, either by a subsequent reaction to introduce a reactive group or bond or by possessing a reactive functional substituent. Thus, the group $R^4$ may advantageously carry one or more substituents for example reactive ester groups such as halogen atoms, e.g. chlorine, bromine or iodine atoms; aromatic or aliphatic sulphonyloxy groups, e.g. mesyloxy or tosyloxy groups; or esterified carboxyl groups e.g. ethoxycarbonyl groups; preferably these are so positioned that they can react with the nitrogen atom of the β-lactam ring, or with a group attached thereto, to form a polycyclic structure such as a cepham, cephem or penam structure.

$R^4$ may also be an acyl group, e.g. an aliphatic, araliphatic or aromatic acyl group wherein the aliphatic, araliphatic or aromatic portion may for example, be as defined above for the hydrocarbyl groups directly attached to the sulphur.

$R^4$ may also form with $R^{2a}$ a divalent hydrocarbyl grouping, that is the sulphur and nitrogen atoms may form part of a ring. When $R^{2a}$ and $R^4$ together constitute an ethylene or substituted ethylene group, the product is a penam; when $R^{2a}$ and $R^4$ together constitute a n-propylene or substituted n-propylene group the product is a cepham.

The copending application of Barton, Underwood, Looker and Hewitt U.S. patent application Ser. No. 167,849, filed July 30, 1971, which has issued as U.S. Pat. No. 3,927,013 on Dec. 16, 1975, describes the addition of an aliphatic, araliphatic or aromatic group to compounds of formula II in which $R^2$ is hydrogen. Compounds of which $R^2$ is a group of formula VI can be converted into their pyrazoline derivatives by reaction with a diazo reagent of the formula $N_2CH\ R^4$ where $R^4$ is an aliphatic, araliphatic or aromatic group. The reaction may be effected in an inert solvent, for example an ether, halogenated hydrocarbon or hydrocarbon solvent, preferably at a temperature between $-15°$ to $+50°$ C., more preferably $-10°$ to $+15°$ C.

According to a still further feature of the invention we provide compounds of the formula

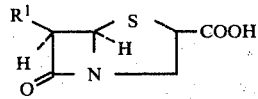

and salts and esters thereof. In particular the isomers 2R,5R,6R-6-phenylacetamido-penam-2-carboxylic acid and 2S,5R,6R-6-phenylacetamidopenam-2-carboxylic acid in the form of their sodium salts have shown activity against penicillin resistant gram positive organisms.

For a better understanding of the invention, the following Examples are given by way of illustration only. All temperatures are in °C. Column chromtography was carried out using Merck 0.05–0.2 mm silica gel. Thin-layer chromatography was carried out on Merck $F_{254}$ plates; the solvents used are given in the individual Examples; NMR spectra were obtained on a Varian HA 100 instrument, unless otherwise stated. The integrals agreed with the numbers of protons indicated. Signs were not determined for the coupling constants (J).

The disulphide starting materials were prepared as described in our copending Application No. 52288/70 of even date herewith (Part 5).

EXAMPLE 1

(3R,4R)-3-Phenylacetamido-4-(2'-chloroethylthio)-acetidin-2-one

A suspension of bis-[(3R,4R)-3-phenylacetamidoazetidin-2-on-4-yl] disulphide (1 g., 2.12 m.mole) in dry methylene chloride (150 ml.) at 0° to 5° was treated with a solution (12 ml., 9.0 m.mole) of chlorine (2 g.) in dry carbon tetrachloride (75 ml.) and stirred until most of the solid had dissolved. Ethylene was passed into the cooled mixture for 30 minutes, then the solution was allowed to warm to room temperature and evaporated to dryness to give a solid.

A solution of the solid was chromatographed on silica gel (3×10 cm) with benzene:ethyl acetate=3:1 as solvent. The major product was collected as a yellow gum which was identified as the title compound. (0.096 g., 7.6%), $\nu_{max}$ (CHBr$_3$), 3410(NH), 1778 (β-lactam), 1676 and 1500 (CONH) cm$^{-1}$, NMR (100 MHz, CDCl$_3$, τ) 2.66 (C$_6$H$_5$), 3.01 (1-NH), 3.34 (CO<u>NH</u>, Doublet, J 9 Hz), 4.47 (double doublet, J 4.5, 3-H) 4.85 (doublet, J 4.5, 4-H), 6.34 (triplet, J 7.5 Hz, CH$_2$—CH$_2$Cl), 6.40 (PhC<u>H</u>$_2$), 6.86 (triplet, J 7.5 Hz, C<u>H</u>$_2$—CH$_2$Cl).

A further quantity (0.64 g.) of the product was obtained, contaminated with a minor component of the reaction mixture.

EXAMPLE 2

(3R,4R)-4-Acetonylthio-3-phenylacetamidoazetidin-2-one (1R,5R)-3-benzyl-4,7-diazo-6-oxo-2-thia-bicyclo [3,2,0]-hept-3-ene (1 g., 0.0046 mole) was heated at 50° with bromoacetone (1.5 ml) in N,N-dimethylformamide (10 ml.) containing water (0.25 ml.), urea (3 g.), and 2,6-di-t-butyl-4-methylphenol (50 mg) (as an anti-oxidant) for 5 hours. The mixture was diluted with ethyl acetate (250 ml.) and washed with water (3×200 ml.) before evaporating the organic solution. The resulting brown gum was chromatographed on silica; elution with ethyl acetate gave (3R4R)-4-acetonylthio-3-phenylacetamidoazetidin-2-one (552 mg., 41%). An analytical sample was obtained by recrystallisation from ethyl acetate, $[\alpha]_D^{20} +28.8°$ (c 1.00, dioxan), m.p. 141°, $\nu_{max}$ (CHBr) 3420 and 3350 (NH), 1170 (β-lactam), 1700 (COCH$_3$), and 1674 and 1506 cm$^{-1}$ (amide), NMR (d$_6$-DMSO, τ) 1.07 (doublet, J 8 Hz; C-3 N<u>H</u>), 1.23 (singlet; β-lactam NH) 2.74 (singlet; phenyl protons), 4.77 (double doublet, J 8. 4 H$_z$; C-3H), 5.13 (doublet, J 4 Hz; C-4H), 6.50 (singlet; PhCH$_2$—), 6.62 (singlet; —SCH$_2$—CO), and 7.90 (singlet; COCH$_3$) [Found: C 57.1; H, 5.4; N, 9.7; S, 10.9; C$_{17}$H$_{16}$N$_2$O S$_3$ (292) requires C, 57.5; H, 5.5; N, 9.6; S, 11.0%].

EXAMPLE 3

S-Alkyl derivatives of 1(R), 5(R)-3-benzyl-4,7-diazo-6-oxo-2-thiabicyclo[3,2,0]-hept-3-ene.

The following S-alkyl derivatives were made in a similar manner to Example 2:

| Halide | R | Solvent | Yield % | Compound |
|---|---|---|---|---|
| BrCH$_2$COOEt | H | DMF/Water | 50 | A |
| ClCH$_2$COPh | H | DMF/Water | 62 | B |
| ClCH$_2$COPh | —CH$_2$COOEt | DMF/Water | 41 | C |
| BrCH$_2$CO—⟨C$_6$H$_4$⟩—Br | H | DMF/Water | 41 | D |
| BrCH$_2$CH=CHCOOEt | H | DMF/Water | 14 | E |
| BrCH$_2$COCH$_2$COOEt | H | DMF/Water | 44 | F |

The constants are as follows:

Compound A

Ethyl (3R,4R)-(3-Phenylacetamidoazetidinon-4-yl)-thioacetate.

Gum, $\nu_{max}$ (CHBr$_3$) 3420 and 3340 (NH), 1778 ($\beta$-lactam), 1728 (ester), and 1680 and 1510 (amide), $\tau$(CDCl$_3$) 2.69 (singlet; phenyl protons), 2.92 (singlet; N-1H), 2.94 (doublet, J 9 Hz, C-3 NH), 4.52 (double doublet, J 9, 4 Hz, C-3H), 4.96 (doublet, J 4 Hz, C-4H), 5.86 (quartet, J 7 Hz, —CH$_2$CH$_3$), 6.40 (singlet; PhCH$_2$—), 6.84 (singlet; —SCH$_2$—), and 8.74 (triplet, J 7 Hz, —CH$_2$CH$_3$).

Compound B (3R,4R)-3-Phenylacetamido-4-phenacylthioazetidin-2-one.

Crystalline solid, M.p. 160° to 162°, [α]$_D^{20}$ ±0° (C 1.00, dioxan), $\nu$max (CHBr$_3$) 3380 and 3300 (two NH groups), 1770 ($\beta$-lactam), 1678 (ketone), and 1678 and 1518 cm$^{-1}$ (amide), $\tau$(d$_6$-DMSO) 0.97 (doublet, J 9 Hz; C-3NH), 1.15 (singlet N-1H), 2.02 to 2.37 (multiplet; CO.Ph), 2.72 (singlet;—CH$_2$Ph), 4.68 (double doublet, J 9,4 Hz; 3-H), 4.99 (doublet, J 4 Hz; 4-H), 5.84 and 6.03 (AB-quartet, J 15 Hz; SCH$_2$), and 6.48 (singlet; —CH$_2$Ph), (Found: C, 63.4; H,5.1; N,7.8; S,8.9. C$_{19}$H$_{18}$N$_2$O$_3$S. 0.25H$_2$O(358.5) requires: C,63.5; H,5.1; N,7.8; S,8.9%).

Compound C

Ethyl (3R,4R)-(3-Phenylacetamido-4-phenacylthioazetidin-2on-1-yl)-acetate.

Crystalline solid, M.p. 110° to 125°, $\nu_{max}$ (CHBr$_3$) 3440 (NH), 1766 ($\beta$-lactam), 1740 (ester), 1690 (ketone), and 1678 and 1510 cm$^{-1}$ (amide), $\tau$(DMSO-d$_6$), 0.98 (singlet; NH), 1.99 to 2.35 (multiplet; COPh), 2.70 (singlet; CH$_2$Ph), 4.66 (double doublet, J 8,5 Hz; 3-H), 4.79 (doublet, J 5 Hz; 4-H), 5.82 (complex; —SCH$_2$, N—CH$_2$, —CH$_2$CH$_3$), 6.46 (singlet; CH$_2$Ph), and 8.76 (triplet; J 7 Hz); —CH$_2$CH$_3$).

Compound D (3R,4R)-4-p-Bromophenacylthio-3-phenylactamidoazetidinone

Crystalline solid, M.p. 160° to 161°, $\nu_{max}$ (CHBr$_3$) 3430 and 3330 (NH), 1780 ($\beta$-lactam), 1680 (ArCO—), and 1680 and 1510 cm.$^{-1}$ (amide).

Compound E

Ethyl 4-(3'R,4'R)-(3'-Phenylacetamidoaxetidinon-4'-yl)-thiocrotonate.

Crystalline solid, M.p. 84° to 87°, [α]$_D^{20}$ −40° (C-1.00, dioxan), $\nu_{max}$ (CHBr$_3$) 3430 and 3380 (two NH groups), 1780 ($\beta$-lactam), 1710 (unsaturated ester), 1676 and 1510 (amide), and 975 cm$^-$(trans-double bond), $\tau$(CDCl$_3$) 2.71 (singlet, phenyl protons), 3.00 (singlet, N-1'H), 3.09 (doublet, J 9 Hz); C-3'NH), 3.18 (double triplet, J 16, 7 Hz; 3-H), 4.15 (doublet, J 16 Hz; 2-H), 4.56 (double doublet, J 9,4.5 Hz; 3'-H), 5.20 (doublet, J 4.5 Hz; 4'-H), 5.80 (quartet, J 7 Hz; CH$_2$CH$_3$), 6.38 (singlet; —CH$_2$Ph), 6.94 (doublet, J 7 Hz; 4-H), and 8.72 (triplet, J 7 Hz; CH$_3$). (Found: C,58.5; H, 5.8; N,8.0; S,9.3. C$_{17}$H$_{20}$N$_2$O$_4$S (348) requires: C,58.5; H5.75; N,8.0; S.9.2%).

Compound F

Ethyl 4-(3'R,4'R)-(3'-Phenylacetaidoazetidinon-4'-yl)-thioaceto acetate.

Crystalline solid, M.p. 60° to 70°, [α]$_D^{20}$ +12.1° (C 1.00, dioxan), $\nu_{max}$ (CHBr$_3$) 3500 (OH), 3408 and 3340 (NH), 1776 ($\beta$-lactam), 1722 (ester), 1720 (ester and carbonyl), and 1679 and 1509 cm$^{-1}$ (amide), $\tau$(DMSO-d$_6$) 1.04 (doublet, J 8 Hz ; CO.NH) 1.20 (singlet; NH), 2.71 (singlet; phenyl protons), 4.75 (double doublet, J 4,8 Hz; C-3H), 5.12 (doublet, J 4 Hz; 4-H), 5.88 (quartet, J 7 Hz; —CH$_2$CH$_3$), 6.35 (singlet; CO.CH$_2$), 6.48 (singlet; PhCH$_2$), 6.70 (singlet; S.CH$_2$), and 8.80 (triplet, J 7 Hz; CH$_2$.CH$_3$). (Found: C,56.0; H, 5.8; N.7.7; S,7.0. CH$_{17}$H$_{21}$N$_2$O$_5$S (365) requires: C,56.0; H,5.7; N,7.7; S,8.7%).

EXAMPLE 4

(3R,4R)-3-Phenylacetamido-4-ethyldithioazetidin-2-one and
(3R,4R)-3-Phenylacetamido-4-ethylthioazetidin-2-one A solution of bis-[(3R,4R)-3-phenylacetamidoazetidin-2-on-4-yl]-disulphide (750 mg., 1.6 m.mole) and ethyl iodide (10 ml. 124 m.mole) in dimethylsulphoxide (30 ml.) at 21° was treated with a solution of sodium sulphide in methanol (4.5 ml of a solution containing 0.83 g. Na$_2$S in 20 ml., 2.4 m.mole). After one minute the solution was diluted with ethyl acetate (100 ml.), washed with water, and then evaporated. The resulting gum was shown by t.l.c. (Merck F$_{254}$ silica gel with benzene:ethyl acetate = 1:1 as solvent) to contain two products Compound A (R$_f$ 0.4) and Compound B (R$_f$ 0.3).

These two compounds were separated by chromatography on silica gel with benzene:ethyl acetate=3:1 as solvents. Compound A, which crystallised from ethyl acetate as colourless prisms, proved to be (3R,4R)-3-phenylacetamido-4-ethyldithio-azetidin-2-one (120 mg., 13%), $\nu_{max}$ (Nujol) 3280 (NH), 1760 ($\beta$-lactam), 1670 and 1530 cm$^{-1}$ (CONH), NMR (CDCl$_3$, $\tau$) 2.72 (C$_6$H$_5$), 3.16

(broad singlet, 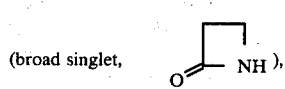

3.42 (doublet, J=9 Hz, CONH), 4.46 (double doublet, J=4.5 and 9 Hz, 3-H), 5.14 (doublet, J=4.5 Hz, 4-H), 6.42 (PhCH$_2$), 7.43 and 8.82 (CH$_2$CH$_3$ respectively) (Found: C, 52.5; H, 5.6; N, 9.7; S, 20.9; C$_{13}$H$_{16}$N$_2$O$_2$S$_2$ requires C, 52.6; H, 5.4; N, 9.4; S, 21.6%). Compound B, which crystallised from ethyl acetate as colourless prisms, proved to be (3R,4R)-3-phenylacetamido-4-ethylthioazetidin-2-one (93 mg., 11%), m.p. 167° to 8°, [$\alpha$]$_D^{21}$ +24° (C 1 tetrahydrofuran), $\nu_{max}$ (Nujol) 3288 (NH), 1760 ($\beta$-lactam), 1671 and 1532 cm$^{-1}$ (CONH), NMR (CDCl$_3$, $\tau$) 2.75 (C$_6$H$_5$), 3.40

(broad singlet, 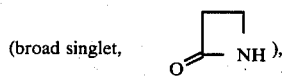

3.63 (doublet, J 9 Hz, CONH), 4.50 (double doublet, J 4.5 and 9 Hz, 3-H), 5.17 (doublet, J 4.5 Hz, 4-H), 6.40 (PhCH$_2$), 7.68 and 8.90 (CH$_2$CH$_3$ respectively). (Found: C, 57.2; H, 6.3; N, 10.2; S, 11.4; C$_{13}$H$_{16}$N$_2$O$_2$S. ½ H$_2$O requires: C, 57.2; H, 6.3; N, 10.5; S, 11.7%).

EXAMPLE 5

(3R,4R)-3-Phenylacetamido-4-ethylthioazetidin-2-one

A solution of bis-[(3R,4R)-3-phenylacetamidoazetidin-2-on-4-yl]-disulphide (0.5 g., 1.06 m.mole) and ethyl iodide (5 ml., 62 m.mole) in N,N-dimethylformamide (10 ml.) at 21° was treated with tri-n-butylphosphine (0.8 ml., 3.15 m.mole). After 10 minutes the solution was diluted with ethyl acetate (50 ml.), washed with water, and evaporated. The resulting gum was chromatographed on silica gel with 2% ethanol in chloroform as solvent and the title compound obtained as a colourless crystalline solid (160 mg., 28.5%), identical in all respects with the material described in Example 4.

EXAMPLE 6

(3R,4R)-3-Phenylacetamido-4-ethylthioazetidin-2-one

A solution of (3R,4R)-4-(2'-methylpropyldithio)-3-phenylacetamidoazetidin-2-one (0.5 g., 1.54 m.mole) and ethyl iodide (0.5 ml., 6.2 m.mole) in N,N-dimethylformamide (10 ml.) was prepared. After 5 minutes the solution was diluted with ethyl acetate (50 ml.), washed with water, and evaporated. The resulting gum was chromatographed on silica gel with benzene: ethyl acetate=3:1, as solvent, and the title compound obtained as a colourless crystalline solid (228 mg., 56%) identical in all respects with the material described in Example 4.

EXAMPLE 7

2',2',2'-Trichloroethyl (3R,4R)-$\alpha$-isopropylidene-$\alpha$-[3-phenylacetamido-4-methylthioazetidin-2-on-1-yl] acetate A solution of 2',2',2'-trichloroethyl (3R,4R)-$\alpha$-isopropylidene-$\alpha$-[3-phenylacetamido-4-(2'-methylpropyl)dithioazetidin-2-on-1-y] acetate (1.00 g. 1.81 m.mole), and freshly redistilled trimethyl phosphite (0.425 ml, 3.62 m.mole) in sodium-dried benzene (50 ml.) was refluxed for 30 minutes. The mixture was evaporated to give an oil, which was purified by precipitation from petroleum ether (b.p. 40° to 60°) yielding, as a foam 2',2',2'-trichloroethyl (3R,4R)-$\alpha$-isopropylidene-$\alpha$-[3-phenyl-acetamido-4-methylthioazetidin-2-on-1-yl] acetate (0.58 g, 67%), $\nu_{max}$ (CHBr$_3$) 3400 (NH), 1765 ($\beta$-lactam), 1735 (unsaturated ester), 1680 (amide), and 1525 cm$^{-1}$ (amide), NMR, (CDCl$_3$ $\tau$) 2.63 (5-proton singlet, phenyl protons), 3.61 (1-proton doublet, J 8 Hz, amide NH), 4.52 (1-proton double doublet, J 4,8 Hz 3-H), 4.74 (1-proton doublet, J 4 Hz, 4-H), 5.21 (2-proton AB-quartet, J 12 Hz, —CH$_2$CCl$_3$), 6.33 (2-proton singlet, —CH$_2$Ph), 7.63 (3-proton singlet, (CH$_3$)), 7.94 (3-proton singlet, (CH$_3$)), and 8.09 (3-proton singlet, —SCH$_3$).

EXAMPLE 8

Methyl (5R,6R)-6-Phenylacetamidopenam-2$\tau$-carboxylate

A solution of bis[(3R,4R)-3-phenylacetamido-1-[(2'-bromo-2'-methoxycarbonyl)ethyl]azetidin-2-on-4-yl] disulphide (0.25 g, 0.31 m.mole) in N,N-dimethylformamide (5 ml.) was treated with tri-n-butylphosphine (0.2 ml. 2.5 equiv.) at 22° for 15 min. The mixture was then poured into water (50 ml.) and extracted with ethyl acetate (25 ml.). After washing with water, drying and evaporation, a gum was obtained. Chromatography on silica (7 g) with benzene:ethyl acetate=4:1 as solvent gave the two products (R$_f$ 0.5 and 0.4 in benzene:ethyl acetate=1:1) as a mixture.

Using fractions containing predominantly less polar product crystallisation was induced by trituration with ether. (40 mg. 20%), m.p. 120° to 121°, IR (CHBr) 3338 (NH), 1775 ($\beta$-lactam), 1725 (CO$_2$R), and 1675 cm$^{-1}$ (CONH), NMR (CDCl$_3$, $\tau$) 2.68 (phenyl), 3.82 (NH), 4.35 and 4.67 (6-H and 5-H respectively AB-quartet J=4 Hz), 5.8 (3-H and 2-H, multiplet), 6.26 (OCH$_3$), 6.39 (CH$_2$ phenyl) and 6.67 (2-H, multiplet) (Found: C, 56.1; H, 4.9; N, 8.6; C$_{15}$H$_{16}$N$_2$O$_4$S requires C, 56.2; H, 5.0; N, 8.8%).

The mother liquor was found to contain predominantly the more polar compound (75 mg. 37%) as an oil, $\nu_{max}$ (CHBr$_3$) 3338 (NH), 1775 ($\beta$-lactam), 1725 (CO$_2$R), and 1675 cm$^{-1}$ (CONH), NMR (CDCl$_3$ $\tau$), 2.68 (phenyl), 3.0 (NH), 4.26 and 4.64 (6-H and 5-H respectively, AB-quartet, J 4 Hz), 5.62 (3-H, doublet, J 14 Hz), 5.93 (2-H doublet J 7 Hz), 6.36 (—CH$_2$ phenyl), 6.40 (OCH$_3$), and 6.90 (3-H, double doublet J 14 and 7 Hz).

EXAMPLE 9 p-Nitrobenzyl (5R,6R)-6-phenylacetamidopenam-2$\xi$-carboxylate

A solution of p-nitrobenzyl-3-[(3'R,4'R)-3'-phenylacetamido-4'-(2''-methylpropyldithio)-azetidin-2'-on-1'-yl]-2-bromopropionate (0.2 g., 0.32 m.mole) in N,N-dimethylformamide (3 ml.) was treated at 22° with tri-n-butylphosphine (0.2 ml. 2.5 equiv.) for 15 minutes. The mixture was then poured into water (25 ml.) and extracted with ethyl acetate (15 ml.). After washing twice with water, drying and evaporating, a foam was obtained. The two products (R$_f$ 0.45 and 0.35, benzene:ethyl acetate=1:1) were isolated as a mixture by chromatography on silica (5 g.) with benzene:ethyl acetate=4:1 as solvent. The less polar compound crystallised from the eluant on evaporation. (29 mg., 19.5%), m.p. 181° to 183°, $\nu_{max}$ (CHBr$_3$) 3415 (NH), 1780 ($\beta$-lactam), 1734 (CO$_2$R), 1672 and 1510 (CONH), and 1522 and 1348 cm$^{-1}$ (Ar.NO$_2$). NMR (CDCl$_3$ $\tau$) 1.75 and 2.45

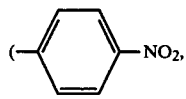

AB-quartet J 9 Hz), 2.2 (NH), 2.55 (phenyl), 4.4 and 4.65 (6-H and 5-H respectively, multiplets, J 4 Hz), 4.7

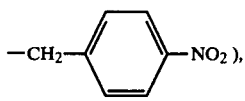

5.6 (2-H,3-H, multiplet,) 6.4 (C$\underline{H}_2$ phenyl), and 6.6 (3-H, multiplet).

The mother-liquor from the above crystallisation contained predominantly the other isomer (R$_f$ 0.35) which was isolated as a gum (70 mg. 41%), $\nu_{max}$ (CHBr$_3$) 3250 (NH), 1790 ($\beta$-lactam), 1738 (CO$_2$R), 1675 and 1500 (—CONH), and 1528 and 1345 cm$^{-1}$ (ArNO$_2$), NMR(CDCl$_3\tau$), 1.75 and 2.55

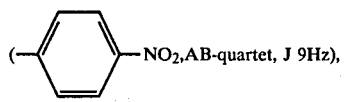

2.65 (Phenyl), 3.1 (NH), 4.25 and 4.65 (6-H and 5-H respectively, AB-quartet, J 4 Hz), 4.9

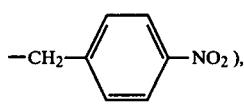

5.7 (2-H and 3-H, multiplet, J 13 and 7 Hz), 6.4 (—C$\underline{H}_2$ phenyl), and 6.85 (3-H, multiplet, J 13 and 7 Hz).

EXAMPLE 10

Reaction of (3R,4R)-4-(2'-methylpropyl)dithio-3-phenylacetamidoazetidin-2-one with ethyl iodide in the presence of tris-(dimethylamino)phosphine A solution of the disulphide (50 mg., 0.17 m.mole) and ethyl iodide (0.1 ml., 1.24 m.mole) in N,N-dimethylformamide at 21° (2 ml.) was treated with tris-(dimethylamino)-phosphine (35 mg., 0.21 m.mole). After 1 minute the solution was diluted with ethyl acetate and this solution washed with water. Thin-layer chromatography of the organic layer revealed the presence of a single product, R$_f$ 0.25. Authentic (3R,4R)-4-ethylthio-3-phenylacetamidoazetidin-2-one also had an R$_f$ 0.25.

EXAMPLE 11 p-Nitrobenzyl 2-[(3'R,4'R)-(3'-Phenylacetamidoazetidin-2'-on-4'-yl)sulphinyl]-acrylate A solution of (1R,5R)-3-benzyl-4, 7-diaza-6-oxo-2-thiabicyclo[3,2,0]-hept-3-ene (0.5 g., 2.3 m.mole) in N,N-dimethylformamide (15 ml.) containing urea (1.5 g., 25 m.mole) and p-nitrobenzyl 2,3-dibromopropionate (0.87 g., 2.5 m.mole) was allowed to stand at 22° for five days. The mixture was poured into excess water and extracted with ethyl acetate (50 ml.). After washing with water, drying and evaporation the crude product was obtained as a foam. Chromatography on silica gel (7 g) using benzene:ethyl acetate=4.1 as solvent gave the title compound (0.12 g., 24%) as an oil, R$_f$ 0.24 (Benzene:ethyl acetate=1:1) $\nu_{max}$ (CHBr$_3$) 3415 (NH), 1772 ($\beta$-lactam), 1722 (ester), 1678 and 1510 (CONH), 1520 and 1350 cm$^{-1}$ (nitro), NMR (CDCl$_3$,$\tau$) 1.76 and 2.47

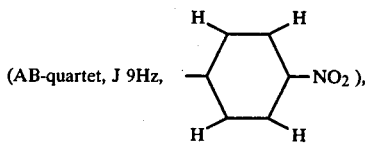

(AB-quartet, J 9Hz, 2.72 (phenyl), 3.15 (two NH groups), 3.57 and 4.30

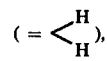

4.37 and 4.93 (3'-H and 4'-H, J 4 Hz), 4.70 (OC$\underline{H}_2$), and 6.43 (C$\underline{H}_2$Ph).

EXAMPLE 12

(3R,4R)-3-Phenylacetamido-4-phenacylthioazetidin-2-one (3R,4R)-4(2'-Methyl-n-propyldithio)-3-phenylacetamidoazetidin-2-one (0.5 g., 0.0015 mole), phenacyl bromide (1.0 g., 0.005 mole), and tributyl phosphine (0.8 ml., 0.0032 mole) were stirred in N,N-dimethylformamide (10 ml.) for 0.25 hours. The reaction mixture was poured into water (100 ml.) and extracted with ethyl acetate (3×100 ml.). The combined organic phases were washed with water (2×100 mls.) and evaporated to a yellow oil which was chromatographed on silica gel eluting with 33% ethyl acetate in benzene to yield (3R,4R)-3-phenylacetamido-4-phenacylthioazetidin-2-one (0.429 g., 78%). The constants were as described previously for compound B in Example 3.

EXAMPLE 13

(a) Benzyl (3'R,4'R)-2-bromo-3 (4'n-butyldithio-3'-phenylacetamidoazetidin-2'-on-1'-yl) propionate To (3R,4R)-4-n-butyldithio-3-phenyl-acetamidoazetidin-2-one (3 g., 9.25 m.mole) in acetone (75 ml.) were added benzyl 2-bromo-acrylate (8.9 g., 37 m.mole) and potassium carbonate (3 g.,), and the mixture was stirred at 21° for 24 hours. After filtration through a pad of Kieselguhr, the mixture was evaporated under reduced pressure to give a brown gum. Chromatography of the gum on silica gel (5×10 cm) with 9:1 benzene:ethyl acetate as solvent gave the title compound (2.3 g., 44%) as a yellow gum, $\nu_{max}$ (CHBr$_3$) 3390 (NH), 1762 ($\beta$-lactam), 1722 and 1242 (—CO$_2$R), 1670 and 1500 cm$^{-1}$ (CONH).

(b) Benzyl [5R,6R]6-Phenylacetamido-penam-2ξ-carboxylate (Isomers A and B)

To a solution of benzyl [3'R,4'R]2-bromo-3(4'-n-butyldithio-3'-phenylacetamidoazetidin-2'-on-1'yl) propionate (17.5 g., 0.031 mole) in N,N-dimethylformamide (350 ml.) was added with stirring a solution of sodium thiosulphate (12.25 g. 0.049 mole) in water (175 ml.) and N,N-dimethylformamide (175 ml.). After stirring at 23° for 10 minutes, the solution was poured into water (2 l.) and extracted with ethyl acetate (4×400 ml.). The ethyl acetate extracts were washed with water (2×500 ml.), dried, and evaporated to a yellow gum which slowly crystallised on standing. Slurrying with 25% ethyl acetate in ether gave Isomer A of the title compound (3.5 g., 28.5%) as colourless prisms, m.p. 130° to 132°, $[\alpha]_D^{22} +266°$ (c, 1.1, tetrahydrofuran), $\nu_{max}$ (CHBr$_3$) 3404 (NH), 1780 ($\beta$-lactam), 1732 (CO$_2$R), and 1678 and 1508 cm$^{-1}$ (CONH), $\tau$(CDCl$_3$), 2.5 to 2.8 (multiplet, PhC$\underline{H}_2$ and CO$_2$CH$_2$P$\underline{h}$), 3.72 (doublet, J 9 Hz, NH), 4.38 (double doublet, J 9 Hz, J 4.5 Hz, 6-H), 4.72 (doublet, J 4.5 Hz, 5-H), 4.84 (singlet, CO$_2$CH$_2$Ph), ABX-system centred at 5.80 and 6.68 (2-H, 3-H and 3'-H) and 6.42 (PhC$\underline{H}_2$) (Found: C, 63.4; H, 5.2; N, 7.0; S, 8.0. C$_{21}$H$_{20}$N$_2$O$_4$S requires, C, 63.4; H, 5.1; N, 7.1; S, 8.1%). After filtering off Isomer A, the filtrate was evaporated to give a brown gum which was chromatographed on silica gel (6×12 cm) with benzene:ethyl acetate=8:1 as solvent. Fractions containing the required product were combined and evaporated to give a yellow gum from which a further sample of Isomer A (0.5 g., 4.5%) slowly crystallised and was filtered off. Evaporation of the filtrate gave Isomer B of the title compound (3.7 g., 30%) as a yellow gum, $[\alpha]_D^{22} +179°$ (C, 0.95, tetrahydrofuran), $\nu_{max}$ (CHBr$_3$) 3370 (NH), 1788 ($\beta$-lactam), 1730 (CO$_2$R), 1676 and 1518 cm$^{-1}$ (CONH), $\tau$ (CDCl$_3$), 2.61 to 2.70 (multiplet, PhC$\underline{H}_2$ and CO$_2$CH$_2$P$\underline{h}$), 3.08 (doublet, J 10 Hz, NH), 4.30 (double doublet, J 10 Hz, J 4 Hz, 6-H), 4.68 (doublet, J 4 Hz, 5-H), 4.92 (CO$_2$C$\underline{H}_2$Ph), 5.62 (doublet, J 13 Hz, 3-H), 5.91 (doublet, J 7 Hz, 2-H), 6.48 (P$\underline{h}$CH$_2$), 6.96 (double doublet, J 13 Hz, J 7 Hz, 3-H). A peak at 4.82$\tau$ indicated the sample to contain 10% of Isomer A.

EXAMPLE 14

Sodium [5R,6R]6-Phenylacetamidopenam-2$\tau$-carboxylate (Isomer A)

To a solution of benzyl [5R,6R]6-phenylacetamido-penam-2-carboxylate (Isomer A) (2.5 g., 0.0063 mole) in ethyl acetate (250 ml) was added 10%-palladium on charcoal (2.5 g., 0.0024 mole) and the mixture was shaken with hydrogen at 24° and atmospheric pressure. After two hours, the catalyst was filtered off, fresh catalyst (2.5 g., 0.0024 mole) added and hydrogenation contained. The catalyst was renewed once more after a further two hours then, after shaking with hydrogen for 30 minutes, the mixture was filtered. Water (200 ml) was added to the filtrate and the stirred mixture was adjusted to pH 7 with saturated aqueous sodium hydrogen carbonate. The aqueous phase was separated and the organic phase extracted with water (1×80 ml), dried, and evaporated under reduced pressure to give the starting ester (0.65 g.). The combined aqueous extracts were washed with ether (1×100 ml.) and freeze-dried to give the Sodium Salt (Isomer A) as a white solid (950 mg, overall yield, 62%). A small sample was further purified by dissolving in acetone, filtering and re-precipitating from ether to give the solid product, $[\alpha]_D^{22} +272°$ (C, 0.99, water), $\nu_{max}$ (Nujol) 3500 (water), 3300 (NH), 1770 ($\beta$-lactam), 1668 and 1550 (CONH), 1608 cm$^{-1}$ (C$\overline{O}_2$), $\tau$(D$_2$O), 2.61 (C$_6$H$_5$), 4.60 (multiplet, 5-H and 6-H), ABX-systems centred at 5.8 and 6.85 (2-H, 3-CH$_2$). (Found: C, 44.7; H, 4.6; N, 7.8; S, 7.9; C$_{14}$H$_{13}$NaN$_2$O$_4$S. 2½H$_2$O requires C, 45.0; H, 4.9; N, 7.5; S, 8.6%), R$_f$ 0.40 (ethyl acetate:n-butanol: 0-1 M Sodium acetate adjusted to pH 5.0=8:1:8) (paper chromatography). In vitro M.I.C. (mcg/ml.) 31 (Staph. aureus 604), 16 (Staph. Aureus 663), 125 (Staph. Aureus 3452), 62 (Staph. Aureus 11127), 250 (H. influenzae 1184E).

EXAMPLE 15

Sodium [5R,6R]-6-Phenylacetamidopenam-2ξ-carboxylate (Isomer B)

To a solution of benzyl [5R,6R]-6-phenylacetamidopenam-2ξ-carboxylate (Isomer B) (2.4 g., 0.00605 mole) in ethyl acetate (240 ml) was added 10%-palladium on charcoal (2.4 g., 0.0023 mole) and the mixture was shaken with hydrogen at 24° and atmospheric pressure. After two hours, the catalyst was filtered off, fresh catalyst (2.4 g., 0.0023 mole) added, and the hydrogenation continued. The catalyst was renewed twice more at two-hour intervals. After finally shaking with hydrogen for 1 hour, the mixture was filtered and water (200 ml.) added to the filtrate. The stirred mixture was adjusted to pH 7 with saturated aqueous sodium hydrogen carbonate, then the aqueous layer was separated and the organic layer extracted with water (1×100 ml), dried, and evaporated. Starting ester (0.93 g.) was obtained as a gum. The combined aqueous phases were washed with ether (1×100 ml.) and freeze-dried to give the Sodium Salt (Isomer B) (0.13 g. overall yield, 10.7%) as an off-white solid $[\alpha]_D^{22} +152°$ (C 0.66, water), $\nu_{max}$ (Nujol) 3300 (NH), 1768 ($\beta$-lactam), 1660 and 1530 (CONH), and 1602 cm$^{-1}$ (C$\overline{O}_2$), $\tau$(CDCl$_3$), 2.62 (P$\underline{h}$CH$_2$), 4.52 and 4.69 (AB-quartet, J 4 Hz, 6-H and 5-H), 5.68 (doublet, J 12 Hz, 3-H), 5.84 (doublet, J 7 Hz, 2-H), 6.32 (PhC$\underline{H}_2$), 6.83

(double doublet, J 12 Hz, J 7 Hz, 3-H), $R_f$ 0.49 (ethyl acetate: n-butanol: 0.1 M Sodium acetate adjusted to pH 5.0=8:1:8) (paper chromatography). In vitro M.I.C. (mcg/ml.) 16 (Staph. Aureus 604), 16 (Staph Aureus 663), 31 (Staph. Aureus 3452), 16 (Staph. Aureus 11127), 250 (H. influenzae 1184 E).

The starting material used in Examples 1, 4 and 5 above may be prepared as described in either Example 7 or Example 8 of the copending application of Barton, Taylor, Underwood, Looker and Hewitt U.S. Pat. application Ser. No. 167,848, filed on July 30, 1971, which issued as U.S. Pat. No. 3,872,086 on Mar. 18, 1975. That used in Examples 6, 10 and 12 may be prepared according to Example 4 of the said copending application and those used in Examples 7, 8, 9 and 13(a) may be prepared according to Examples 1, 9, 6 and 10 respectively of the said copending application.

The starting material for Examples 2, 3 and 11 may be prepared as described in Example 1(c) of the copending application of Barton, Long, Looker, Wilson and Underwood U.S. Ser. No. 167,876, filed July 30, 1971, now U.S. Pat. No. 3,991,069.

We claim:
1. A process for the preparation of compounds of formula IV:

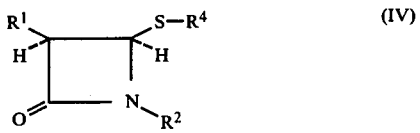

wherein $R^1$ is a phenylacetamido or phenoxyacetamido group; $R^2$ is a hydrogen atom or a group of formula:

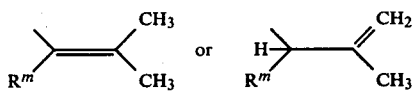

wherein $R^m$ is hydrogen, esterified hydroxyl, etherified hydroxyl, carboxyl or esterified carboxyl; and $R^4$ is an alkyl group containing 1 to 6 carbon atoms which comprises the step of reacting a compound of formula II:

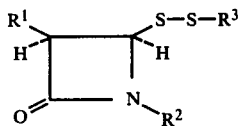

wherein $R^1$ and $R^2$ have the above meanings and $R^3$ is an alkyl group containing 1 to 6 carbon atoms or a group of the formula III wherein $R^1$ and $R^2$ are as defined:

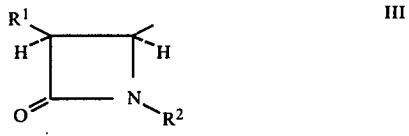

with a trivalent phosphorus compound of formula $PR^5R^6R^7$ wherein $R^5$, $R^6$ and $R^7$ which may be the same or different are selected from the group consisting of $C_{1-6}$ alkyl and di-$C_{1-6}$ alkylamino groups, in the presence of a reagent $R^4X$ wherein $R^4$ has the above meaning and X is a halogen atom.

2. The process as claimed in claim 1, wherein the trivalent phosphorous compound is tributyl phosphine.

3. The process of claim 1, wherein the reaction is carried out at a temperature of between 0° and 120° C.

4. The process of claim 1, wherein $R^m$ is tetrahydropyranyloxy, 4-methoxytetrahydropyranyloxy, di-(2-chloroethoxy)-methoxy, diphenylmethoxy, carbobenzoxy or trifluoroacetoxy.

5. The process of claim 1, wherein $R^m$ is 2,2,2-trichloroethoxy, 2,2,2-trichloro-1-methylethoxy, 2,2,2-tribromoethoxy or 2-iodoethoxy.

6. The process of claim 1, wherein the compound of formula II is:

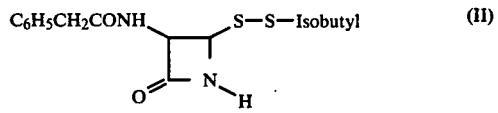

and cleaved to yield:

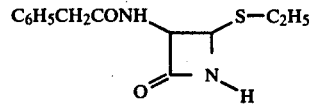

7. The process of claim 1, wherein $R^3$ is the group of formula III.

8. The process of claim 1, wherein $R^3$ is an alkyl group containing 1 to 6 carbon atoms.

9. The process of claim 1, wherein the phosphorus compound is $P(NMe_2)_3$.

* * * * *